(12) United States Patent
Frisbee et al.

(10) Patent No.: US 12,263,301 B2
(45) Date of Patent: *Apr. 1, 2025

(54) LOAD-BASED DETECTION OF AN AEROSOL DELIVERY DEVICE IN AN ASSEMBLED ARRANGEMENT

(71) Applicant: RAI Strategic Holdings, Inc., Winston-Salem, NC (US)

(72) Inventors: Mark Frisbee, Raleigh, NC (US); Paul Stapleton, Apex, NC (US); Milton G. Carawan, Cary, NC (US); Frederic Philippe Ampolini, Winston-Salem, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 33 days.

This patent is subject to a terminal disclaimer.

(21) Appl. No.: 18/320,786

(22) Filed: May 19, 2023

(65) Prior Publication Data

US 2023/0285696 A1  Sep. 14, 2023

Related U.S. Application Data

(60) Continuation of application No. 17/190,091, filed on Mar. 2, 2021, now Pat. No. 11,684,732, which is a
(Continued)

(51) Int. Cl.
*A61M 15/06* (2006.01)
*A24F 40/10* (2020.01)
(Continued)

(52) U.S. Cl.
CPC ............. *A61M 15/06* (2013.01); *A24F 40/40* (2020.01); *A24F 40/50* (2020.01); *A61M 11/042* (2014.02);
(Continued)

(58) Field of Classification Search
CPC ........ A24F 40/40; A24F 40/50; A24F 47/008; A24F 47/002; A61M 15/06;
(Continued)

(56) References Cited

U.S. PATENT DOCUMENTS 1,771,366 A   7/1930   Wyss et al.
2,057,353 A   10/1936  Whittemore, Jr.
(Continued)

FOREIGN PATENT DOCUMENTS

AU      276250       7/1965
CA    2 641 869      5/2010
(Continued)

OTHER PUBLICATIONS

International Search Report for International Application No. PCT/US2016/042215, dated Oct. 7, 2016.

*Primary Examiner* — Steven W Crabb
*Assistant Examiner* — Alba T Rosario-Aponte
(74) *Attorney, Agent, or Firm* — Womble Bond Dickinson (US) LLP

(57) ABSTRACT

A control body is coupleable with a cartridge to form an aerosol delivery device, with the cartridge being equipped with an electrical load. The control body includes first and second positive conductors connectable with respectively a power supply and the electrical load. The control body includes a series pull-up resistor and switch connected to and between the first and second positive conductors. A microprocessor is configured to operate the switch in a closed state in a standby mode in which the pull-up resistor causes a logical high level of voltage at the second positive conductor when the control body and cartridge are uncoupled, and in which the electrical load is unpowered causes a logical low level of the voltage when the control body and cartridge are coupled. The microprocessor is
(Continued)

configured to measure the voltage and control operation of functional element(s) of the aerosol delivery device based thereon.

11 Claims, 8 Drawing Sheets

Related U.S. Application Data division of application No. 14/802,137, filed on Jul. 17, 2015, now Pat. No. 10,966,460.

(51) Int. Cl.
| | |
|---|---|
| *A24F 40/40* | (2020.01) |
| *A24F 40/50* | (2020.01) |
| *A61M 11/04* | (2006.01) |
| *H05B 1/02* | (2006.01) |
| *H05B 3/00* | (2006.01) |

(52) U.S. Cl.
CPC ......... *H05B 1/0202* (2013.01); *H05B 1/0244* (2013.01); *H05B 3/0014* (2013.01); *A24F 40/10* (2020.01); *A61M 2205/14* (2013.01); *A61M 2205/3334* (2013.01); *A61M 2205/3653* (2013.01); *A61M 2205/50* (2013.01); *A61M 2205/502* (2013.01); *A61M 2205/6018* (2013.01); *A61M 2205/6027* (2013.01); *A61M 2205/8206* (2013.01)

(58) Field of Classification Search
CPC . A61M 11/042; H05B 1/0202; H05B 1/0244; H05B 3/0014
USPC .......................... 392/387, 386, 390, 394–398
See application file for complete search history.

(56) References Cited

U.S. PATENT DOCUMENTS

| | | |
|---|---|---|
| 2,104,266 A | 1/1938 | McCormick |
| 3,200,819 A | 8/1965 | Gilbert |
| 4,284,089 A | 8/1981 | Ray |
| 4,303,083 A | 12/1981 | Burruss, Jr. |
| 4,735,217 A | 4/1988 | Gerth et al. |
| 4,848,374 A | 7/1989 | Chard et al. |
| 4,907,606 A | 3/1990 | Lilja et al. |
| 4,922,901 A | 5/1990 | Brooks et al. |
| 4,945,931 A | 8/1990 | Gori |
| 4,947,874 A | 8/1990 | Brooks et al. |
| 4,947,875 A | 8/1990 | Brooks et al. |
| 4,986,286 A | 1/1991 | Roberts et al. |
| 5,019,122 A | 5/1991 | Clearman et al. |
| 5,042,510 A | 8/1991 | Curtiss et al. |
| 5,060,671 A | 10/1991 | Counts et al. |
| 5,093,894 A | 3/1992 | Deevi et al. |
| 5,144,962 A | 9/1992 | Counts et al. |
| 5,249,586 A | 10/1993 | Morgan et al. |
| 5,261,424 A | 11/1993 | Sprinkel, Jr. |
| 5,322,075 A | 6/1994 | Deevi et al. |
| 5,353,813 A | 10/1994 | Deevi et al. |
| 5,369,723 A | 11/1994 | Counts et al. |
| 5,372,148 A | 12/1994 | McCafferty et al. |
| 5,388,574 A | 2/1995 | Ingebrethsen et al. |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,530,225 A | 6/1996 | Hajaligol |
| 5,564,442 A | 10/1996 | MacDonald et al. |
| 5,649,554 A | 7/1997 | Sprinkel et al. |
| 5,666,977 A | 9/1997 | Higgins et al. |
| 5,687,746 A | 11/1997 | Rose et al. |
| 5,726,421 A | 3/1998 | Fleischhauer et al. |
| 5,727,571 A | 3/1998 | Meiring et al. |
| 5,743,251 A | 4/1998 | Howell et al. |
| 5,799,663 A | 9/1998 | Gross et al. |
| 5,819,756 A | 10/1998 | Mielordt |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,934,289 A | 8/1999 | Watkins et al. |
| 5,954,979 A | 9/1999 | Counts et al. |
| 5,967,148 A | 10/1999 | Harris et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,125,853 A | 10/2000 | Susa et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,772,756 B2 | 8/2004 | Shayan |
| 6,803,545 B2 | 10/2004 | Blake et al. |
| 6,854,461 B2 | 2/2005 | Nichols |
| 6,854,470 B1 | 2/2005 | Pu |
| 7,117,867 B2 | 10/2006 | Cox et al. |
| 7,293,565 B2 | 11/2007 | Griffin et al. |
| 7,513,253 B2 | 4/2009 | Kobayashi et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,127,772 B2 | 3/2012 | Montaser |
| 8,314,591 B2 | 11/2012 | Terry et al. |
| 8,365,742 B2 | 2/2013 | Hon |
| 8,402,976 B2 | 3/2013 | Fernando et al. |
| 8,499,766 B1 | 8/2013 | Newton |
| 8,528,569 B1 | 9/2013 | Newton |
| 8,550,069 B2 | 10/2013 | Alelov |
| 11,684,732 B2 * | 6/2023 | Frisbee ................. A61M 15/06 392/404 |
| 2002/0146242 A1 | 10/2002 | Vieira |
| 2003/0226837 A1 | 12/2003 | Blake et al. |
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2006/0016453 A1 | 1/2006 | Kim |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2008/0085103 A1 | 4/2008 | Beland et al. |
| 2008/0092912 A1 | 4/2008 | Robinson et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0095311 A1 | 4/2009 | Hon |
| 2009/0095312 A1 | 4/2009 | Herbrich et al. |
| 2009/0126745 A1 | 5/2009 | Hon |
| 2009/0188490 A1 | 7/2009 | Hon |
| 2009/0230117 A1 | 9/2009 | Fernando et al. |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0043809 A1 | 2/2010 | Magnon |
| 2010/0083959 A1 | 4/2010 | Siller |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036363 A1 | 2/2011 | Urtsev et al. |

(56) References Cited

U.S. PATENT DOCUMENTS

| | | |
|---|---|---|
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0192619 A1 | 8/2013 | Tucker et al. |
| 2013/0255702 A1 | 10/2013 | Griffith, Jr. et al. |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0157583 A1 | 6/2014 | Ward et al. |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0299141 A1* | 10/2014 | Flick ............... H05B 1/0202 219/494 |
| 2014/0345631 A1 | 11/2014 | Bowen et al. |
| 2015/0053217 A1 | 2/2015 | Steingraber et al. |
| 2015/0101625 A1* | 4/2015 | Newton ............. A24F 40/60 131/329 |
| 2015/0173124 A1 | 6/2015 | Qiu |
| 2016/0374397 A1* | 12/2016 | Jordan ............. G01L 19/0092 131/329 |
| 2018/0103686 A1* | 4/2018 | Monsees ............. A24F 40/40 |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| CN | 102940313 | 2/2013 |
| CN | 204217894 | 3/2015 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| GB | 2469850 | 11/2010 |
| JP | H05-265616 | 10/1993 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2013/089551 | 6/2013 |
| WO | WO 2014/150247 | 9/2014 |
| WO | WO 2014/205694 | 12/2014 |
| WO | WO 2015/052513 | 4/2015 |

* cited by examiner

LOAD-BASED DETECTION OF AN AEROSOL DELIVERY DEVICE IN AN ASSEMBLED ARRANGEMENT

CROSS-REFERENCE TO RELATED APPLICATIONS

The present application is a continuation of U.S. patent application Ser. No. 17/190,091, filed Mar. 2, 2021, which is a divisional of U.S. patent application Ser. No. 14/802,137, entitled: Load-Based Detection of an Aerosol Delivery Device in an Assembled Arrangement, filed Jul. 17, 2015, the content of which are hereby incorporated by reference.

TECHNOLOGICAL FIELD

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from, or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar or pipe smoking, but without delivering considerable quantities of incomplete combustion and pyrolysis products that result from the burning of tobacco. To this end, there have been proposed numerous smoking products, flavor generators and medicinal inhalers that utilize electrical energy to vaporize or heat a volatile material, or attempt to provide the sensations of cigarette, cigar or pipe smoking without burning tobacco to a significant degree. See, for example, the various alternative smoking articles, aerosol delivery devices and heat generating sources set forth in the background art described in U.S. Pat. No. 7,726,320 to Robinson et al., U.S. Pat. App. Pub. No. 2013/0255702 to Griffith Jr. et al., and U.S. Pat. App. Pub. No. 2014/0096781 to Sears et al., all of which are incorporated herein by reference in their entireties. See also, for example, the various types of smoking articles, aerosol delivery devices and electrically-powered heat generating sources referenced by brand name and commercial source in U.S. patent application Ser. No. 14/170,838 to Bless et al., filed Feb. 3, 2014, which is incorporated herein by reference in its entirety. Additionally, other types of smoking articles have been proposed in U.S. Pat. No. 5,505,214 to Collins et al., U.S. Pat. No. 5,894,841 to Voges, U.S. Pat. No. 6,772,756 to Shayan, U.S. Pat. App. Pub. No. 2006/0196518 to Hon, and U.S. Pat. App. Pub. No. 2007/0267031 to Hon, all of which are incorporated herein by reference in their entireties. One example of a popular type of so-called e-cigarette has been commercially available under the trade name VUSE™ by RJ Reynolds Vapor Company.

It would be desirable to provide a smoking article that employs heat produced by electrical energy to provide the sensations of cigarette, cigar, or pipe smoking, that does so without combusting or pyrolyzing tobacco to any significant degree, that does so without the need of a combustion heat source, and that does so without necessarily delivering considerable quantities of incomplete combustion and pyrolysis products. Further, advances with respect to manufacturing electronic smoking articles would be desirable.

SUMMARY

The present disclosure relates to aerosol delivery devices, methods of forming such devices, and elements of such devices. The present disclosure includes, without limitation, the following example implementations. In some example implementations, a control body is provided. The control body is coupleable with a cartridge that is equipped with an electrical load and contains an aerosol precursor composition, the control body being coupleable with the cartridge to form an aerosol delivery device in which the electrical load is configured to activate and vaporize components of the aerosol precursor composition. The control body comprises a first positive conductor connectable with a power supply; a second positive conductor connectable with the electrical load; a series pull-up resistor and switch connected to and between the first positive conductor and second positive conductor, the switch being connected to and between the pull-up resistor and second positive conductor; and a microprocessor configured to operate the switch in a closed state in a standby mode in which the pull-up resistor is configured to cause a logical high level of voltage at the second positive conductor when the control body is uncoupled with the cartridge, and in which the electrical load is unpowered and causes a logical low level of the voltage at the second positive conductor when the control body is coupled with the cartridge, wherein the microprocessor is configured to measure the voltage at the second positive conductor and control operation of at least one functional element of the aerosol delivery device based thereon.

In some example implementations of the control body of the preceding or any subsequent example implementation, or any combination thereof, the microprocessor being configured to control operation of the at least one functional element includes being configured to control operation of the at least one functional element in response to a coupling of the control body with the cartridge that causes the voltage at the second positive conductor to decrease from the logical high level to the logical low level.

In some example implementations of the control body of any preceding or any subsequent example implementation, or any combination thereof, the microprocessor being configured to control operation of the at least one functional element includes being configured to control operation of the at least one functional element in response to an uncoupling of the control body with the cartridge that causes the voltage at the second positive conductor to increase from the logical low level to the logical high level.

In some example implementations of the control body of any preceding or any subsequent example implementation, or any combination thereof, the microprocessor being configured to control operation of at least one functional element includes being configured to control operation of at least one visual, audio or haptic indicator.

In some example implementations of the control body of any preceding or any subsequent example implementation, or any combination thereof, the control body further comprises a voltage divider connected to and between the second positive conductor and microprocessor, referenced to ground, and from which the microprocessor is configured to measure the voltage at the second positive conductor.

In some example implementations of the control body of any preceding or any subsequent example implementation, or any combination thereof, the control body further comprises a second switch connected to and between the voltage divider and ground, the microprocessor being configured to operate the second switch in an open state in the standby mode.

In some example implementations of the control body of any preceding or any subsequent example implementation, or any combination thereof, the voltage divider includes an output connected to the microprocessor and from which the microprocessor is configured to measure the voltage at the second positive conductor, and the control body further comprises a capacitor connected to and between the output and ground.

In some example implementations of the control body of any preceding or any subsequent example implementation, or any combination thereof, the microprocessor is further configured to operate the switch in an open state in an active mode in which the control body is coupled with the cartridge, the microprocessor is configured to direct power to the electrical load to activate and vaporize components of the aerosol precursor composition, and in which the voltage at the second positive conductor corresponds to a positive electrical load voltage, and wherein in the active mode, the microprocessor is configured to measure the positive electrical load voltage and control the power directed to the electrical load based thereon.

In some example implementations of the control body of any preceding or any subsequent example implementation, or any combination thereof, the control body further comprises a voltage divider connected to and between the second positive conductor and microprocessor, referenced to ground, and from which the microprocessor is configured to measure the positive electrical load voltage; and a second switch connected to and between the voltage divider and ground, the microprocessor being configured to operate the second switch in a closed state in the active mode.

In some example implementations of the control body of any preceding or any subsequent example implementation, or any combination thereof, the microprocessor being configured to direct power to the electrical load and control the power directed to the electrical load includes being configured to at least: direct power from a power source to turn the electrical load on and commensurately initiate a loading time period; and at a periodic rate until expiration of the loading time period, determine a moving window of measurements of instantaneous actual power directed to the electrical load, each measurement of the window of measurements being determined as a product of the positive electrical load voltage and a current through the electrical load; calculate a simple moving average power directed to the electrical load based on the moving window of measurements of instantaneous actual power; compare the simple moving average power to a selected power set point associated with the power source; and adjust the power directed to the electrical load so as to turn the electrical load off or on at the periodic rate at each instance in which the simple moving average power is respectively above or below the selected power set point.

In some example implementations of the control body of any preceding or any subsequent example implementation, or any combination thereof, the electrical load comprises a heating element.

In some example implementations, a method is provided for controlling a control body coupleable with a cartridge that is equipped with an electrical load and contains an aerosol precursor composition, the control body being coupleable with the cartridge to form an aerosol delivery device in which the electrical load is configured to activate and vaporize components of the aerosol precursor composition, the control body including a first positive conductor connectable with a power supply, a second positive conductor connectable with the electrical load, and a series pull-up resistor and switch connected to and between the first positive conductor and second positive conductor, the switch being connected to and between the pull-up resistor and second positive conductor. The method comprises operating the switch in a closed state in a standby mode in which the pull-up resistor is configured to cause a logical high level of voltage at the second positive conductor when the control body is uncoupled with the cartridge, and in which the electrical load is unpowered causes a logical low level of the voltage at the second positive conductor when the control body is coupled with the cartridge; measuring the voltage at the second positive conductor; and controlling operation of at least one functional element of the aerosol delivery device based on the voltage measured at the second positive conductor.

In some example implementations of the method of the preceding or any subsequent example implementation, or any combination thereof, controlling operation of the at least one functional element includes controlling operation of the at least one functional element in response to a coupling of the control body with the cartridge that causes the voltage at the second positive conductor to decrease from the logical high level to the logical low level.

In some example implementations of the method of any preceding or any subsequent example implementation, or any combination thereof, controlling operation of the at least one functional element includes controlling operation of the at least one functional element in response to an uncoupling of the control body with the cartridge that causes the voltage at the second positive conductor to increase from the logical low level to the logical high level.

In some example implementations of the method of any preceding or any subsequent example implementation, or any combination thereof, controlling operation of at least one functional element includes controlling operation of at least one visual, audio or haptic indicator.

In some example implementations of the method of any preceding or any subsequent example implementation, or any combination thereof, the control body further includes a voltage divider connected to the second positive conductor and referenced to ground, and wherein measuring the voltage at the second positive conductor includes measuring the voltage from the voltage divider.

In some example implementations of the method of any preceding or any subsequent example implementation, or any combination thereof, the control body further includes a second switch connected to and between the voltage divider and ground, and wherein the method further comprises operating the second switch in an open state in the standby mode.

In some example implementations of the method of any preceding or any subsequent example implementation, or any combination thereof, the voltage divider includes an output, and the control body further comprises a capacitor connected to and between the output and ground, and wherein measuring the voltage at the second positive conductor includes measuring the voltage from the output of the voltage divider.

In some example implementations of the method of any preceding or any subsequent example implementation, or any combination thereof, the method further comprises operating the switch in an open state in an active mode in which the control body is coupled with the cartridge; and in which the method further comprises, directing power to the electrical load to activate and vaporize components of the aerosol precursor composition, and in which the voltage at the second positive conductor corresponds to a positive electrical load voltage; measuring the positive electrical load voltage; and controlling the power directed to the electrical load based thereon.

In some example implementations of the method of any preceding or any subsequent example implementation, or any combination thereof, the control body further includes a voltage divider connected to the second positive conductor and referenced to ground, and includes a second switch connected to and between the voltage divider and ground, wherein measuring the positive electrical load voltage includes measuring the positive electrical load voltage from the voltage divider, and wherein the method further comprises operating the second switch in a closed state in the active mode.

In some example implementations of the method of any preceding or any subsequent example implementation, or any combination thereof, directing power to the electrical load and controlling the power directed to the electrical load includes at least: directing power from a power source to turn the electrical load on and commensurately initiate a loading time period; and at a periodic rate until expiration of the loading time period, determining a moving window of measurements of instantaneous actual power directed to the electrical load, each measurement of the window of measurements being determined as a product of the positive electrical load voltage and a current through the electrical load; calculating a simple moving average power directed to the electrical load based on the moving window of measurements of instantaneous actual power; comparing the simple moving average power to a selected power set point associated with the power source; and adjusting the power directed to the electrical load so as to turn the electrical load off or on at the periodic rate at each instance in which the simple moving average power is respectively above or below the selected power set point.

In some example implementations of the method of any preceding or any subsequent example implementation, or any combination thereof, the electrical load comprises a heating element, and operating the switch comprises operating the switch in a closed state in a standby mode in which the heating element is unpowered.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE DRAWING(S)

Having thus described the disclosure in the foregoing general terms, reference will now be made to the accompanying drawings, which are not necessarily drawn to scale, and wherein:

DETAILED DESCRIPTION

Figure 1:
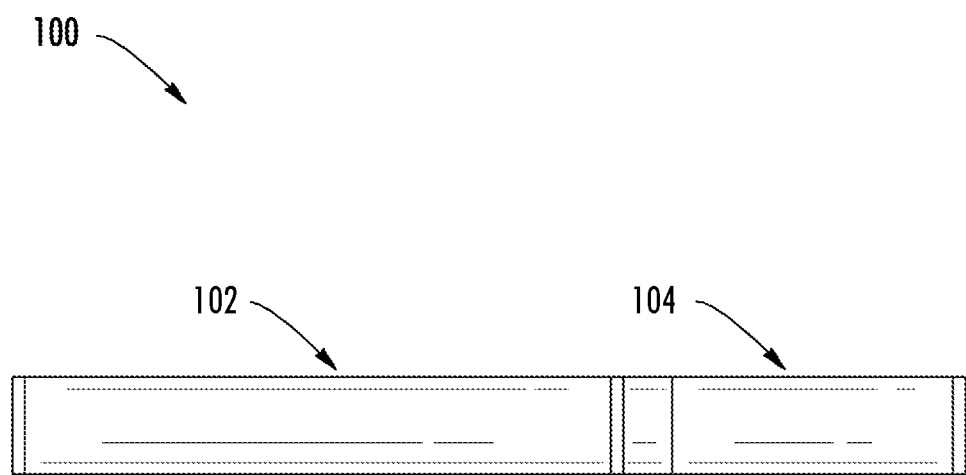
FIG. 1 illustrates a side view of an aerosol delivery device including a cartridge coupled to a control body according to an example implementation of the present disclosure.

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise.

As described hereinafter, example implementations of the present disclosure relate to aerosol delivery systems. Aerosol delivery systems according to the present disclosure use electrical energy to heat a material (preferably without combusting the material to any significant degree) to form an inhalable substance; and components of such systems have the form of articles most preferably are sufficiently compact to be considered hand-held devices. That is, use of components of preferred aerosol delivery systems does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery systems of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

Aerosol delivery systems of the present disclosure generally include a number of components provided within an outer body or shell, which may be referred to as a housing. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary housing or the elongated housing can be formed of two or more separable bodies. For example, an aerosol delivery device can comprise an elongated shell or body that can be substantially tubular in shape and, as such, resemble the shape of a conventional cigarette or cigar. In one example, the aerosol delivery device can comprise two or more housings that are joined and are separable. For example, an aerosol delivery device can possess at one end a control body comprising a housing containing one or more reusable components (e.g., a rechargeable battery and various electronics for controlling the operation of that article), and at the other end and removably coupleable thereto, an outer body or shell containing a disposable portion (e.g., a disposable flavor-containing cartridge).

Aerosol delivery systems of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microprocessor, individually or as part of a microcontroller), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

In various examples, an aerosol delivery device can comprise a reservoir configured to retain the aerosol precursor composition. The reservoir particularly can be formed of a porous material (e.g., a fibrous material) and thus may be referred to as a porous substrate (e.g., a fibrous substrate).

A fibrous substrate useful as a reservoir in an aerosol delivery device can be a woven or nonwoven material formed of a plurality of fibers or filaments and can be formed of one or both of natural fibers and synthetic fibers. For example, a fibrous substrate may comprise a fiberglass material. In particular examples, a cellulose acetate material can be used. In other example implementations, a carbon material can be used. A reservoir may be substantially in the form of a container and may include a fibrous material included therein.

FIG. 1 illustrates a side view of an aerosol delivery device 100 including a control body 102 and a cartridge 104, according to various example implementations of the present disclosure. In particular, FIG. 1 illustrates the control body and the cartridge coupled to one another. The control body and the cartridge may be detachably aligned in a functioning relationship. Various mechanisms may connect the cartridge to the control body to result in a threaded engagement, a press-fit engagement, an interference fit, a magnetic engagement or the like. The aerosol delivery device may be substantially rod-like, substantially tubular shaped, or substantially cylindrically shaped in some example implementations when the cartridge and the control body are in an assembled configuration. The cartridge and control body may include separate, respective housings or outer bodies, which may be formed of any of a number of different materials. The housing may be formed of any suitable, structurally-sound material. In some examples, the housing may be formed of a metal or alloy, such as stainless steel, aluminum or the like. Other suitable materials include various plastics (e.g., polycarbonate), metal-plating over plastic and the like.

In some example implementations, one or both of the control body 102 or the cartridge 104 of the aerosol delivery device 100 may be referred to as being disposable or as being reusable. For example, the control body may have a replaceable battery or a rechargeable battery and thus may be combined with any type of recharging technology, including connection to a typical alternating current electrical outlet, connection to a car charger (i.e., a cigarette lighter receptacle), and connection to a computer, such as through a universal serial bus (USB) cable or connector. Further, in some example implementations, the cartridge may comprise a single-use cartridge, as disclosed in U.S. Pat. No. 8,910, 639 to Chang et al., which is incorporated herein by reference in its entirety.

Figure 2:
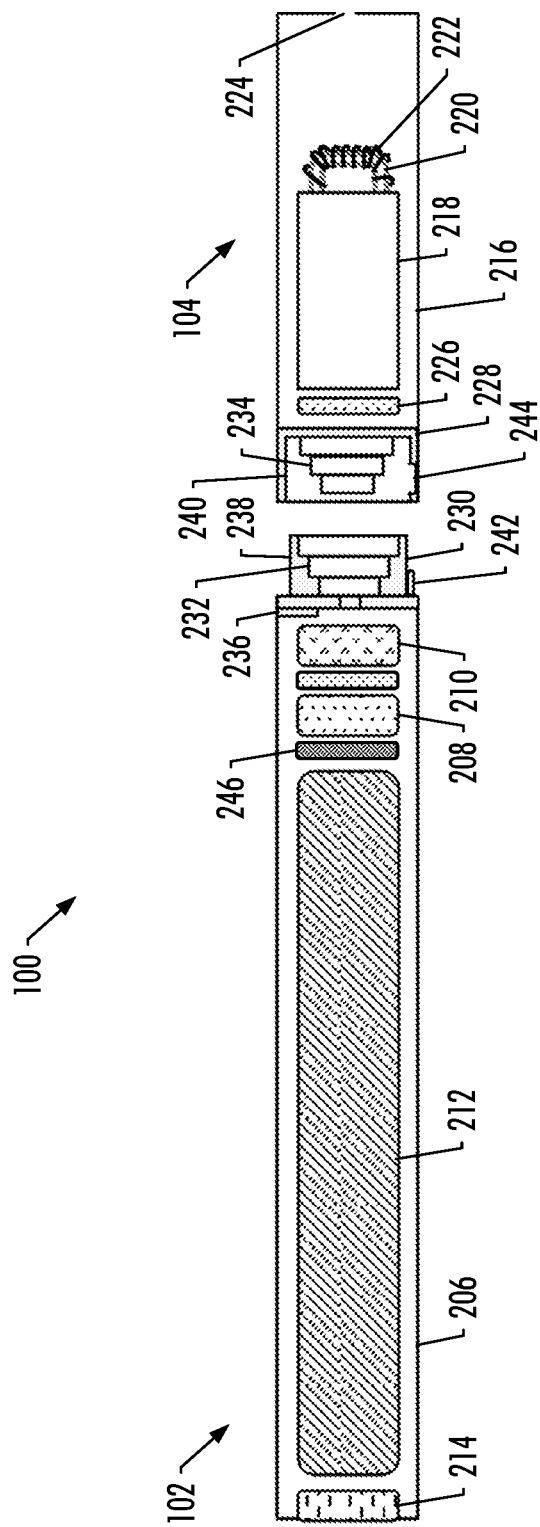
FIG. 2 is a partially cut-away view of the aerosol delivery device according to various example implementations.

FIG. 2 more particularly illustrates the aerosol delivery device 100, in accordance with some example implementations. As seen in the cut-away view illustrated therein, again, the aerosol delivery device can comprise a control body 102 and a cartridge 104. As illustrated in FIG. 2, the control body can be formed of a control body shell 206 that can include a control component 208 (e.g., a microprocessor, individually or as part of a microcontroller), a flow sensor 210, a battery 212 and one or more light-emitting diodes (LEDs)

214, and such components can be variably aligned. The LED may be one example of a suitable visual indicator with which the aerosol delivery device 100 may be equipped. Other indicators such as audio indicators (e.g., speakers), haptic indicators (e.g., vibration motors) or the like can be included in addition to or as an alternative to visual indicators such as the LED.

The cartridge 104 can be formed of a cartridge shell 216 enclosing a reservoir 218 that is in fluid communication with a liquid transport element 220 adapted to wick or otherwise transport an aerosol precursor composition stored in the reservoir housing to a heater 222 (sometimes referred to as a heating element). In some example, a valve may be positioned between the reservoir and heater, and configured to control an amount of aerosol precursor composition passed or delivered from the reservoir to the heater.

Various examples of materials configured to produce heat when electrical current is applied therethrough may be employed to form the heater 222. The heater in these examples may be resistive heating element such as a wire coil. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials (e.g., carbon-based foams and yarns) and ceramics (e.g., positive or negative temperature coefficient ceramics). Example implementations of heaters or heating members useful in aerosol delivery devices according to the present disclosure are further described below, and can be incorporated into devices such as illustrated in FIG. 2 as described herein.

An opening 224 may be present in the cartridge shell 216 (e.g., at the mouthend) to allow for egress of formed aerosol from the cartridge 104. Such components are representative of the components that may be present in a cartridge and are not intended to limit the scope of cartridge components that are encompassed by the present disclosure.

The cartridge 104 also may include one or more electronic components 226, which may include an integrated circuit, a memory component, a sensor, or the like. The electronic components may be adapted to communicate with the control component 208 and/or with an external device by wired or wireless means. The electronic components may be positioned anywhere within the cartridge or a base 228 thereof.

Although the control component 208 and the flow sensor 210 are illustrated separately, it is understood that the control component and the flow sensor may be combined as an electronic circuit board with the air flow sensor attached directly thereto. Further, the electronic circuit board may be positioned horizontally relative the illustration of FIG. 1 in that the electronic circuit board can be lengthwise parallel to the central axis of the control body. In some examples, the air flow sensor may comprise its own circuit board or other base element to which it can be attached. In some examples, a flexible circuit board may be utilized. A flexible circuit board may be configured into a variety of shapes, include substantially tubular shapes. In some examples, a flexible circuit board may be combined with, layered onto, or form part or all of a heater substrate as further described below.

The control body 102 and the cartridge 104 may include components adapted to facilitate a fluid engagement therebetween. As illustrated in FIG. 2, the control body can include a coupler 230 having a cavity 232 therein. The base 228 of the cartridge can be adapted to engage the coupler and can include a projection 234 adapted to fit within the cavity. Such engagement can facilitate a stable connection between the control body and the cartridge as well as establish an electrical connection between the battery 212 and control component 208 in the control body and the heater 222 in the cartridge. Further, the control body shell 206 can include an air intake 236, which may be a notch in the shell where it connects to the coupler that allows for passage of ambient air around the coupler and into the shell where it then passes through the cavity 232 of the coupler and into the cartridge through the projection 234.

A coupler and a base useful according to the present disclosure are described in U.S. Pat. App. Pub. No. 2014/0261495 to Novak et al., which is incorporated herein by reference in its entirety. For example, the coupler 230 as seen in FIG. 2 may define an outer periphery 238 configured to mate with an inner periphery 240 of the base 228. In one example the inner periphery of the base may define a radius that is substantially equal to, or slightly greater than, a radius of the outer periphery of the coupler. Further, the coupler may define one or more protrusions 242 at the outer periphery configured to engage one or more recesses 244 defined at the inner periphery of the base. However, various other examples of structures, shapes and components may be employed to couple the base to the coupler. In some examples the connection between the base of the cartridge 104 and the coupler of the control body 102 may be substantially permanent, whereas in other examples the connection therebetween may be releasable such that, for example, the control body may be reused with one or more additional cartridges that may be disposable and/or refillable.

The aerosol delivery device 100 may be substantially rod-like or substantially tubular shaped or substantially cylindrically shaped in some examples. In other examples, further shapes and dimensions are encompassed—e.g., a rectangular or triangular cross-section, multifaceted shapes, or the like.

The reservoir 218 illustrated in FIG. 2 can be a container or can be a fibrous reservoir, as presently described. For example, the reservoir can comprise one or more layers of nonwoven fibers substantially formed into the shape of a tube encircling the interior of the cartridge shell 216, in this example. An aerosol precursor composition can be retained in the reservoir. Liquid components, for example, can be sorptively retained by the reservoir. The reservoir can be in fluid connection with the liquid transport element 220. The liquid transport element can transport the aerosol precursor composition stored in the reservoir via capillary action to the heater 222 that is in the form of a metal wire coil in this example. As such, the heater is in a heating arrangement with the liquid transport element. Example implementations of reservoirs and transport elements useful in aerosol delivery devices according to the present disclosure are further described below, and such reservoirs and/or transport elements can be incorporated into devices such as illustrated in FIG. 2 as described herein. In particular, specific combinations of heating members and transport elements as further described below may be incorporated into devices such as illustrated in FIG. 2 as described herein.

In use, when a user draws on the aerosol delivery device 100, airflow is detected by the flow sensor 210, and the heater 222 is activated to vaporize components of the aerosol precursor composition. Drawing upon the mouthend of the aerosol delivery device causes ambient air to enter the air intake 236 and pass through the cavity 232 in the coupler 230 and the central opening in the projection 234 of the base 228. In the cartridge 104, the drawn air combines with the formed vapor to form an aerosol. The aerosol is whisked, aspirated or otherwise drawn away from the heater and out the opening 224 in the mouthend of the aerosol delivery device.

In some examples, the aerosol delivery device 100 may include a number of additional software-controlled functions. For example, the aerosol delivery device may include a battery protection circuit configured to detect battery input, loads on the battery terminals, and charging input. The battery protection circuit may include short-circuit protection and under-voltage lock out. The aerosol delivery device may also include components for ambient temperature measurement, and its control component 208 may be configured to control at least one functional element to inhibit battery charging if the ambient temperature is below a certain temperature (e.g., 0° C.) or above a certain temperature (e.g., 45° C.) prior to start of charging or during charging.

Power delivery from the battery 212 may vary over the course of each puff on the device 100 according to a power control mechanism. The device may include a "long puff" safety timer such that in the event that a user or an inadvertent mechanism causes the device to attempt to puff continuously, the control component 208 may control at least one functional element to terminate the puff automatically after some period of time (e.g., four seconds). Further, the time between puffs on the device may be restricted to less than a period of time (e.g., 100). A watchdog safety timer may automatically reset the aerosol delivery device if its control component or software running on it becomes unstable and does not service the timer within an appropriate time interval (e.g., eight seconds). Further safety protection may be provided in the event of a defective or otherwise failed flow sensor 210, such as by permanently disabling the aerosol delivery device in order to prevent inadvertent heating. A puffing limit switch may deactivate the device in the event of a pressure sensor fail causing the device to continuously activate without stopping after the four second maximum puff time.

The aerosol delivery device 100 may include a puff tracking algorithm configured for heater lockout once a defined number of puffs has been achieved for an attached cartridge (based on the number of available puffs calculated in light of the e-liquid charge in the cartridge). The aerosol delivery device may include a sleep, standby or low-power mode function whereby power delivery may be automatically cut off after a defined period of non-use. Further safety protection may be provided in that all charge/discharge cycles of the battery 212 may be monitored by the control component 208 over its lifetime. After the battery has attained the equivalent of a predetermined number (e.g., 200) full discharge and full recharge cycles, it may be declared depleted, and the control component may control at least one functional element to prevent further charging of the battery.

The various components of an aerosol delivery device according to the present disclosure can be chosen from components described in the art and commercially available. Examples of batteries that can be used according to the disclosure are described in U.S. Pat. App. Pub. No. 2010/0028766 to Peckerar et al., which is incorporated herein by reference in its entirety.

The aerosol delivery device 100 can incorporate the sensor 210 or another sensor or detector for control of supply of electric power to the heater 222 when aerosol generation is desired (e.g., upon draw during use). As such, for example, there is provided a manner or method of turning off the power supply to the heater when the aerosol delivery device is not be drawn upon during use, and for turning on the power supply to actuate or trigger the generation of heat by the heater during draw. Additional representative types of sensing or detection mechanisms, structure and configuration thereof, components thereof, and general methods of operation thereof, are described in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference in their entireties.

The aerosol delivery device 100 most preferably incorporates the control component 208 or another control mechanism for controlling the amount of electric power to the heater 222 during draw. Representative types of electronic components, structure and configuration thereof, features thereof, and general methods of operation thereof, are described in U.S. Pat. No. 4,735,217 to Gerth et al., U.S. Pat. No. 4,947,874 to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. App. Pub. No. 2009/0230117 to Fernando et al., U.S. Pat. App. Pub. No. 2014/0060554 to Collet et al., U.S. Pat. App. Pub. No. 2014/0270727 to Ampolini et al., and U.S. patent application Ser. No. 14/209,191 to Henry et al., filed Mar. 13, 2014, all of which are incorporated herein by reference in their entireties.

Representative types of substrates, reservoirs or other components for supporting the aerosol precursor are described in U.S. Pat. No. 8,528,569 to Newton, U.S. Pat. App. Pub. No. 2014/0261487 to Chapman et al., U.S. patent application Ser. No. 14/011,992 to Davis et al., filed Aug. 28, 2013, and U.S. patent application Ser. No. 14/170,838 to Bless et al., filed Feb. 3, 2014, all of which are incorporated herein by reference in their entireties. Additionally, various wicking materials, and the configuration and operation of those wicking materials within certain types of electronic cigarettes, are set forth in U.S. Pat. App. Pub. No. 2014/0209105 to Sears et al., which is incorporated herein by reference in its entirety.

The aerosol precursor composition, also referred to as a vapor precursor composition, may comprise a variety of components including, by way of example, a polyhydric alcohol (e.g., glycerin, propylene glycol or a mixture thereof), nicotine, tobacco, tobacco extract and/or flavorants. Various components that may be included in the aerosol precursor composition are described in U.S. Pat. No. 7,726,320 to Robinson et al., which is incorporated herein by reference in its entirety. Additional representative types of aerosol precursor compositions are set forth in U.S. Pat. No. 4,793,365 to Sensabaugh, Jr. et al., U.S. Pat. No. 5,101,839 to Jakob et al., U.S. Pat. No. 6,779,531 to Biggs et al., U.S. Pat. App. Pub. No. 2013/0008457 to Zheng et al., and *Chemical and Biological Studies on New Cigarette Prototypes that Heat Instead of Burn Tobacco*, R. J. Reynolds Tobacco Company Monograph (1988), all of which are incorporated herein by reference in their entireties.

Additional representative types of components that yield visual cues or indicators may be employed in the aerosol delivery device 100, such as visual indicators and related components, audio indicators, haptic indicators and the like. Examples of suitable LED components, and the configurations and uses thereof, are described in U.S. Pat. No. 5,154,192 to Sprinkel et al., U.S. Pat. No. 8,499,766 to Newton, U.S. Pat. No. 8,539,959 to Scatterday, and U.S. patent application Ser. No. 14/173,266 to Sears et al., filed Feb. 5, 2014, all of which are incorporated herein by reference in their entireties.

Yet other features, controls or components that can be incorporated into aerosol delivery devices of the present disclosure are described in U.S. Pat. No. 5,967,148 to Harris et al., U.S. Pat. No. 5,934,289 to Watkins et al., U.S. Pat. No. 5,954,979 to Counts et al., U.S. Pat. No. 6,040,560 to Fleischhauer et al., U.S. Pat. No. 8,365,742 to Hon, U.S. Pat. No. 8,402,976 to Fernando et al., U.S. Pat. App. Pub. No. 2005/0016550 to Katase, U.S. Pat. App. Pub. No. 2010/0163063 to Fernando et al., U.S. Pat. App. Pub. No. 2013/0192623 to Tucker et al., U.S. Pat. App. Pub. No. 2013/0298905 to Leven et al., U.S. Pat. App. Pub. No. 2013/0180553 to Kim et al., U.S. Pat. App. Pub. No. 2014/0000638 to Sebastian et al., U.S. Pat. App. Pub. No. 2014/0261495 to Novak et al., and U.S. Pat. App. Pub. No. 2014/0261408 to DePiano et al., all of which are incorporated herein by reference in their entireties.

The control component 208 includes a number of electronic components, and in some examples may be formed of a printed circuit board (PCB) that supports and electrically connects the electronic components. The electronic components may include a microprocessor or processor core, and a memory. In some examples, the control component may include a microcontroller with integrated processor core and memory, and which may further include one or more integrated input/output peripherals. In some examples, the control component may be coupled to a communication interface to enable wireless communication with one or more networks, computing devices or other appropriately-enabled devices. Examples of suitable communication interfaces are disclosed in U.S. patent application Ser. No. 14/638,562, filed Mar. 4, 2015, to Marion et al., the content of which is incorporated by reference in its entirety. And examples of suitable manners according to which the aerosol delivery device may be configured to wirelessly communicate are disclosed in U.S. patent application Ser. No. 14/327,776, filed Jul. 10, 2014, to Ampolini et al., and U.S. patent application Ser. No. 14/609,032, filed Jan. 29, 2015, to Henry, Jr. et al., each of which is incorporated herein by reference in its entirety.

Figure 3:
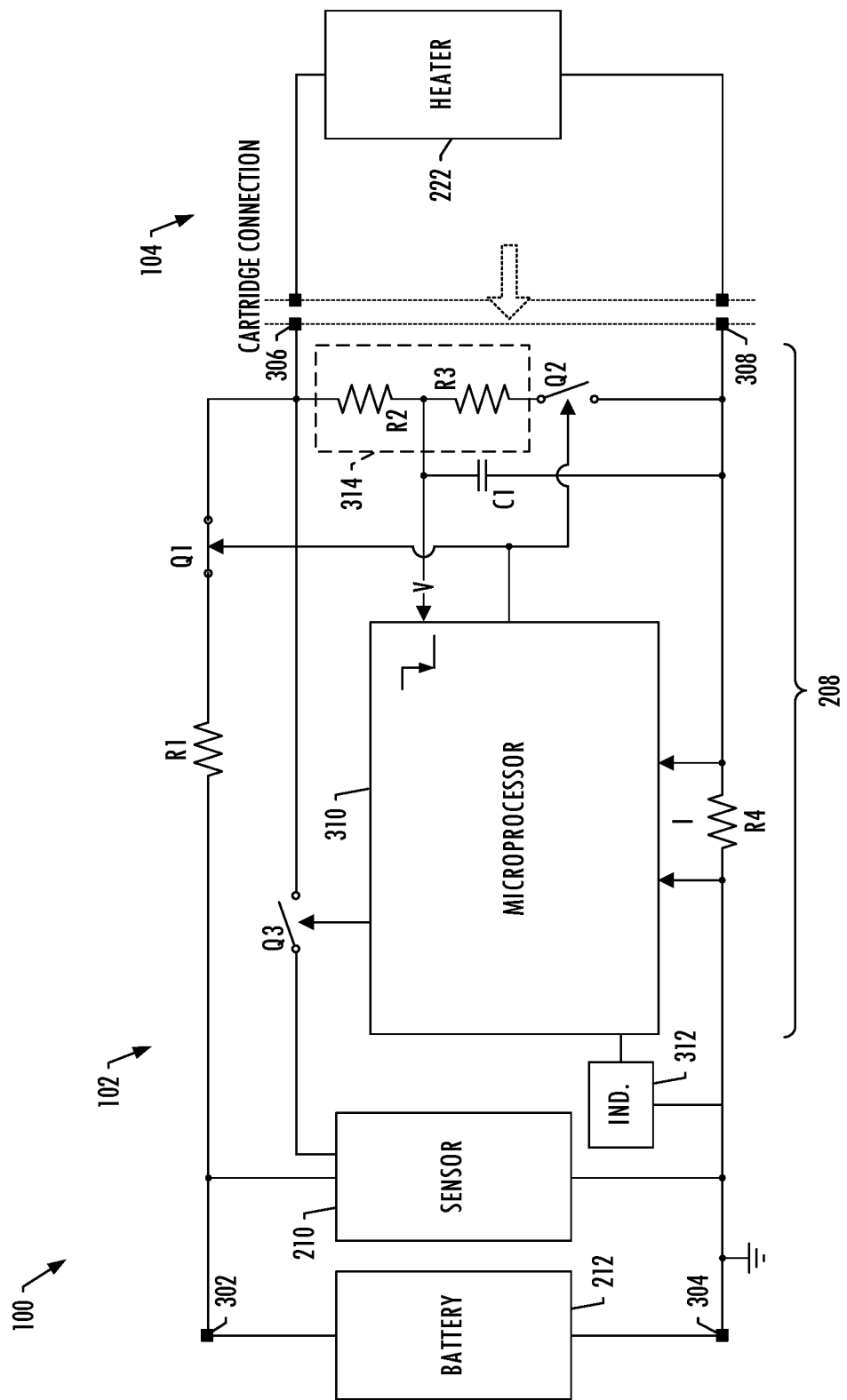
FIGS. 3-7 illustrate various elements of a control body and cartridge of the aerosol delivery device, according to various example implementations.
Figure 4:
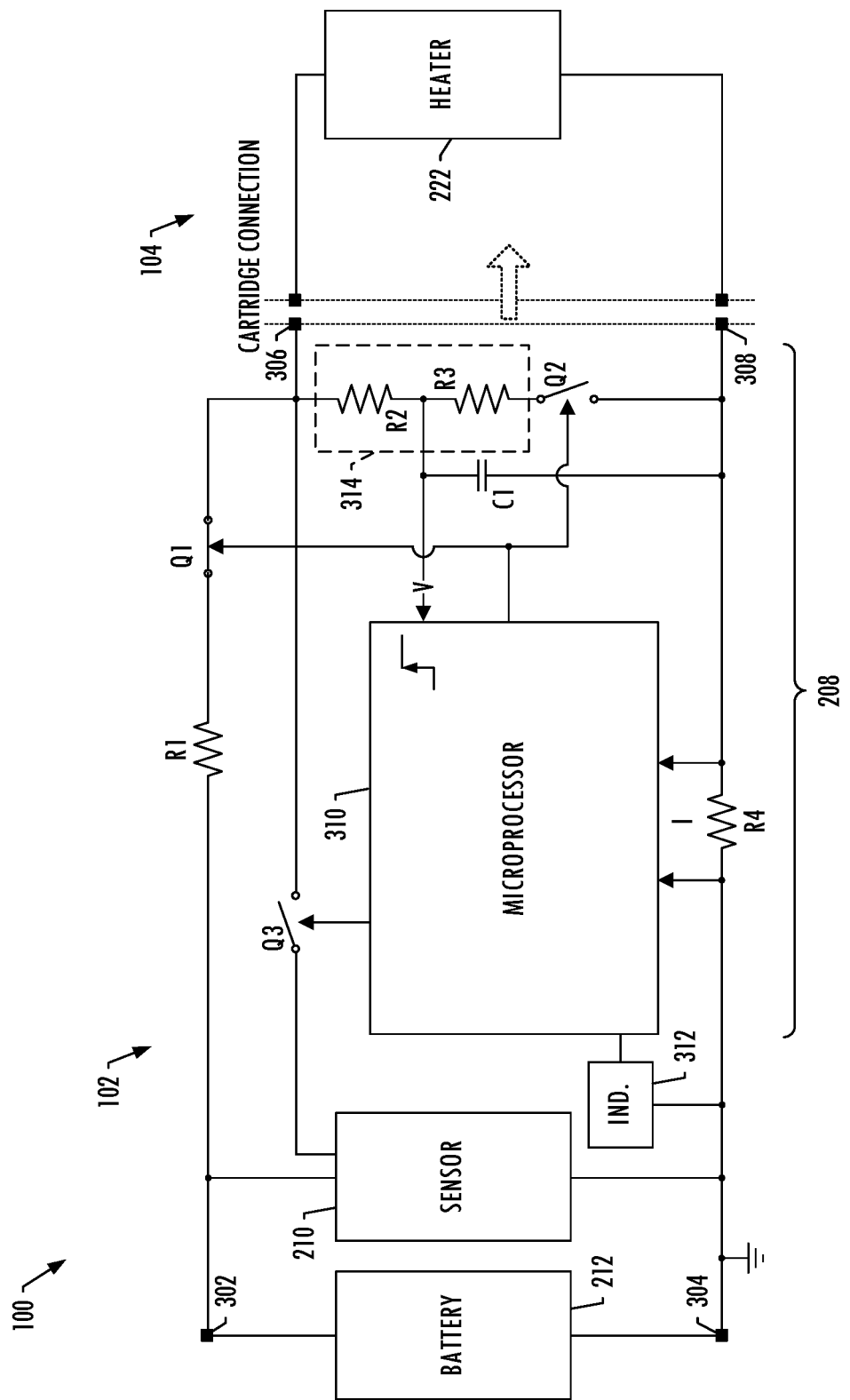

In accordance with some example implementations, the control component 208 may be configured to control of one or more functional elements of the aerosol delivery device 100 in different states of the device, and depending on whether the control body 102 is coupled or uncoupled with the cartridge 104. For example, the control component may be configured to control one or more components that yield visual cues or indicators in response to a coupling of the control body with the cartridge, and/or in response to an uncoupling of the control body with the cartridge. FIGS. 3 and 4 illustrate a coupling and uncoupling of the control body with the cartridge in a standby mode, and FIG. 5 illustrates the control body coupled with the cartridge in an active mode.

Figure 5:
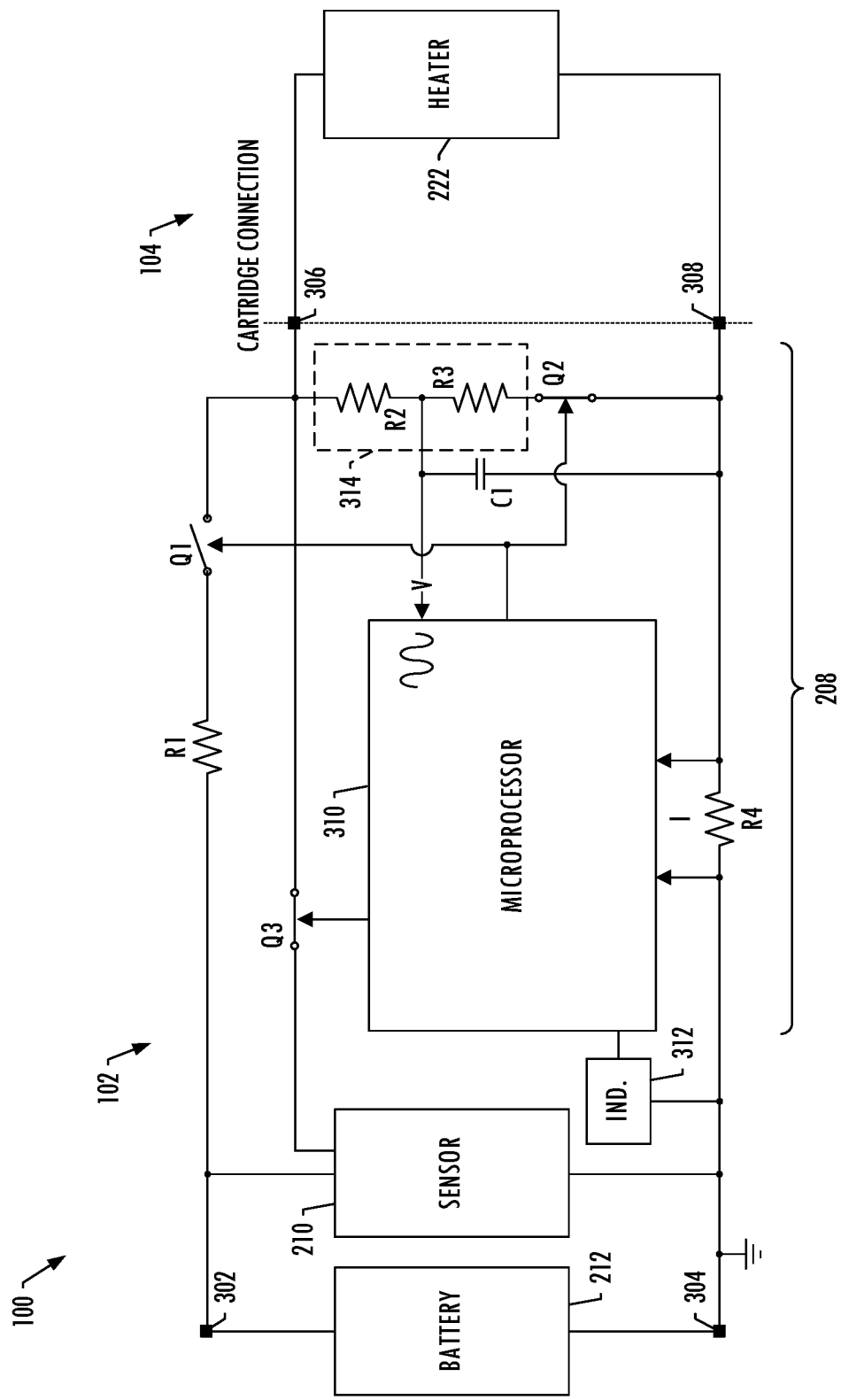

As shown in FIGS. 3-5, the control body 102 may include a (first) positive conductor 302 and a (first) negative conductor 304 connectable with the battery 212 (power supply). The control body may likewise include a (second) positive conductor 306 and a (second) negative conductor 308 connectable with the heater 222 (heating element). The control component 208 may include a microprocessor 310 and a number of electrical components, such as resistors, capacitors, switches and the like, which may be coupled with the battery and heater to form an electrical circuit. As shown, for example, the control component may include a series pull-up resistor R1 and switch Q1 connected to and between the first positive conductor and second positive conductor, with the switch being connected to and between the pull-up resistor and second positive conductor.

The microprocessor 310 may be configured to operate the switch Q1 in a closed state in a standby mode in which the pull-up resistor R1 is configured to cause a logical high level of voltage at the second positive conductor 306 when the control body 102 is uncoupled with the cartridge 104. Also in the standby mode, the heater 222 may be unpowered and cause a logical low level of the voltage at the second positive conductor when the control body is coupled with the cartridge. That is, when the control body is uncoupled with the cartridge, the pull-up resistor may be configured to pull the voltage at the second positive conductor toward the positive battery (power supply) voltage for the logical high level. When the control body is coupled with the cartridge, on the other hand, the voltage at the second positive conductor may correspond to an approximately zero positive heater voltage for the logical low level. In this instance, the heater in the standby mode is essentially a short to the second negative conductor 308. A voltage divider may be formed between R1 (e.g., 10 s of k$\Omega$) and the heater resistance (e.g., <10 $\Omega$), which may result in a positive heater voltage at the second positive conductor of approximately zero volts.

In accordance with example implementations of the present disclosure, the microprocessor 310 may be configured to measure the voltage at the second positive conductor 306 and control operation of at least one functional element of the aerosol delivery device 100 based thereon. In some examples, the microprocessor may operate on the actual voltage at the second positive conductor, or the control component 208 or microprocessor may include an analog-to-digital converter (ADC) configured to convert the actual voltage to a digital equivalent.

As shown in FIG. 3, in one example, the microprocessor 310 may be configured to control operation of a functional element in response to a coupling of the control body 102 with the cartridge 104 that causes the voltage at the second positive conductor 306 to decrease from the logical high level to the logical low level. In another example, as shown in FIG. 4, the microprocessor may be configured to control operation of a functional element in response to an uncoupling of the control body with the cartridge that causes the voltage at the second positive conductor to increase from the logical low level to the logical high level. In either example, the functional element may be an indicator 312 such as a visual, audio or haptic indicator.

In some examples, the microprocessor 310 may include an ADC configured to convert the actual voltage to a digital equivalent, and this ADC may be rated for a maximum voltage less than the maximum that may be present at the second positive conductor 306. In these examples, the control component 208 may further include a voltage divider 314 configured to reduce the voltage to the microprocessor. As shown, for example, the voltage divider may include resistors R2 and R3, and may be connected to and between the second positive conductor and microprocessor, referenced to ground. The microprocessor may be configured to measure the voltage at the second positive conductor from the voltage divider. In this regard, the voltage divider may include an output connected to the microprocessor and from which the microprocessor may be configured to measure the voltage at the second positive conductor. The control component of the control body may further include a capacitor C1 connected to and between the output and ground. And further, the control component may include a second switch Q2 connected to and between the voltage divider and ground, which the microprocessor may be configured to operate in an open state in the standby mode.

The aerosol delivery device 100 and more particularly the control component 102 may be in the standby mode when the control component is uncoupled with the cartridge 104. Similarly, the aerosol delivery device may be in the standby mode when the control component is coupled with the cartridge between puffs on the device. When the user draws on the device and the flow sensor 210 detects airflow, the aerosol delivery device may be placed in the active mode during which power from the battery 212 may be directed through the sensor to power the heater 222 to activate and vaporize components of the aerosol precursor composition. In another example, power from the battery may more directly power the heater without going through the sensor (without the sensor being in-line), although the flow sensor may still detect airflow when the user draws on the device. As indicated above, power delivery from the battery 212 may vary according to a power control mechanism; and in some examples, this power control mechanism may depend on a measured voltage at the second positive conductor 306.

As shown in FIG. 5, in the active mode in which the control body 102 is coupled with the cartridge 104, the microprocessor 310 may be configured to operate the switch Q1 in an open state, and operate the second switch Q2 in a closed state. In this mode, the microprocessor may be configured to direct power to the heater 222 to activate and vaporize components of the aerosol precursor composition. The voltage at the second positive conductor 306 may correspond to a positive heater voltage. The microprocessor may be configured to measure the positive heater voltage, such as from the voltage divider 314, and control the power directed to the heater based thereon.

In some more particular examples, the microprocessor 310 may be configured to direct power from the battery 212 (e.g., directly or through the flow sensor 210) to turn the heater 222 on and commensurately initiate a heating time period. This may include, for example, a further switch Q3 between the battery (or in-line flow sensor) and the heater, which the microprocessor may operate in a closed state, as shown in FIG. 5. The microprocessor may then adjust the power directed to the heater based on the voltage at the second positive conductor 306, at a periodic rate until expiration of the heating time period.

In some examples, this adjustment of power directed to the heater 222 may include the microprocessor 310 being configured to determine a moving window of measurements of instantaneous actual power directed to the heater, with each measurement of the window of measurements being determined as a product of the positive heater voltage and a current through the heater. This current may be measured in a number of different manners, such as from a current-sense resistor R4. In some examples, the microprocessor may operate on the actual current through the heater, or the control component 208 or microprocessor may include an ADC configured to convert the actual current to a digital equivalent.

The microprocessor 310 may calculate a simple moving average power directed to the heater 222 based on the moving window of measurements of instantaneous actual power, and compare the simple moving average power to a selected power set point associated with the battery 212. The microprocessor may then adjust the power directed to the heater so as to turn the heater off or on at the periodic rate at each instance in which the simple moving average power is respectively above or below the selected power set point. More information regarding aspects of the control component according to example implementations of the present disclosure may be found in the above-cited and incorporated U.S. Pat. App. Pub. No. 2014/0270727 to Ampolini et al.

Figure 6:
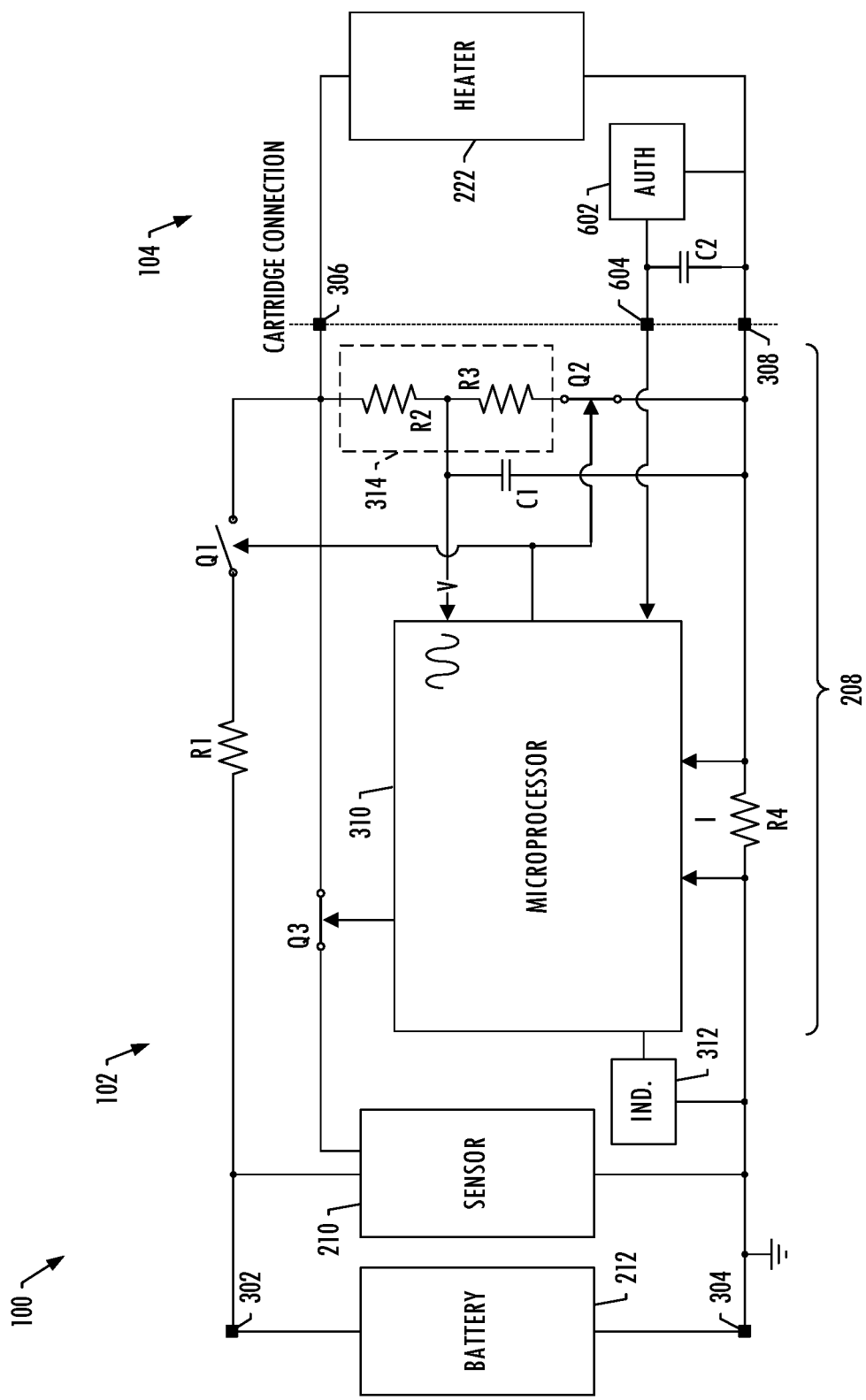

As shown in FIG. 6, in some examples, the cartridge 104 may also include an authentication device 602 (e.g., a Texas Instruments Model bq26150 authentication IC) to deter or prevent counterfeit cartridges from being used with the control body 102. The control body may include a (third) positive conductor 604 connectable with an output of the authentication device, from which the microprocessor may be configured to authenticate the cartridge for use with the control body. The cartridge may further include a capacitor C2 connected to and between the output of the authentication device and ground. Although not separately shown, an additional memory unit associated with the authentication device may be used to store a depletion amount of the cartridge unit, as well as to store other programmable features and information associated with the cartridge unit. Again, more information regarding authentication according to aspects of the present disclosure may be found in the above-cited and incorporated U.S. Pat. App. Pub. No. 2014/0270727 to Ampolini et al.

Figure 7:
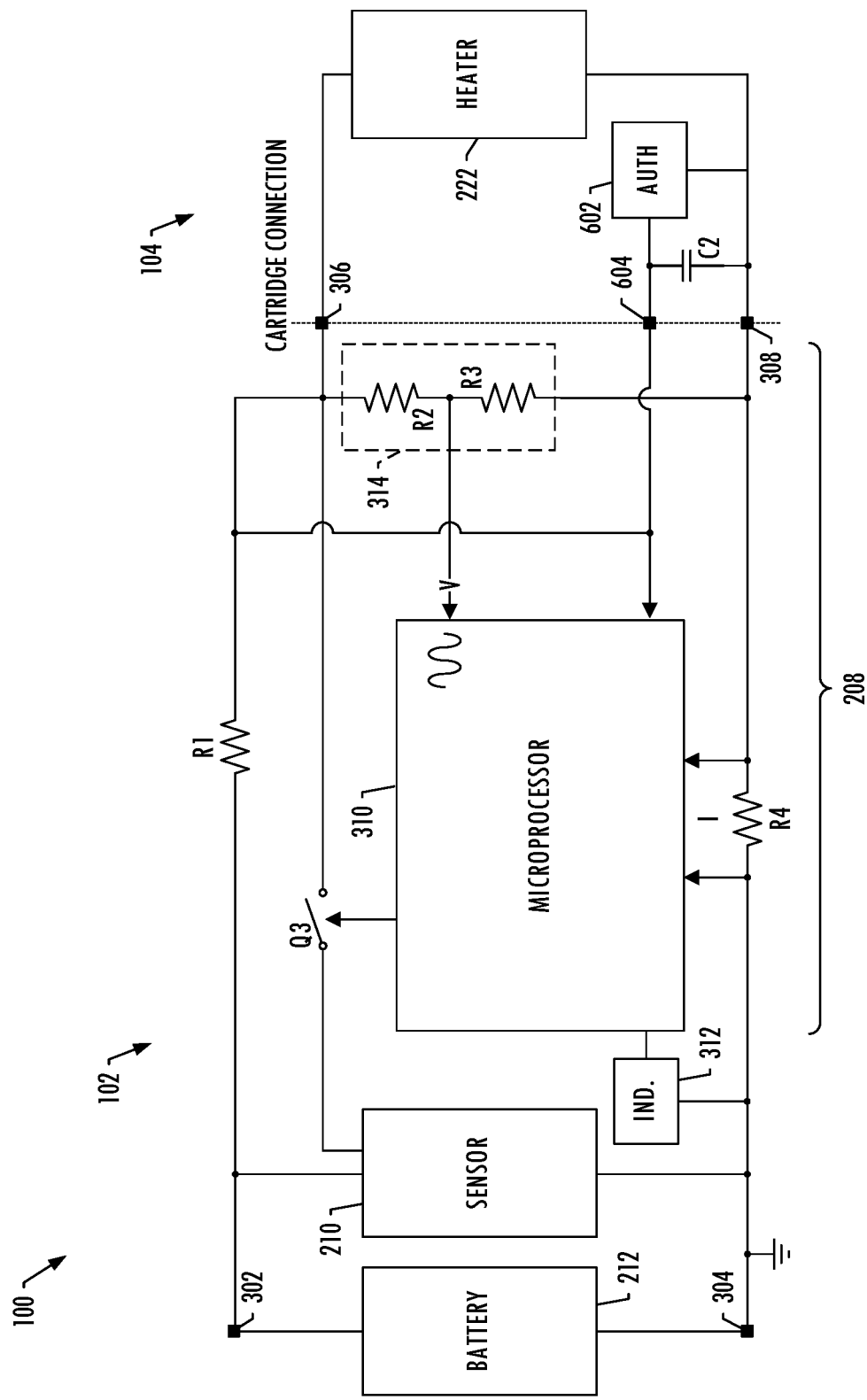

In some even further examples, the authentication device 602 instead of the heater 222 may be further useful for the microprocessor 310 to control operation of the functional element (e.g., indicator 312) in response to at least a coupling of the control body 102 with the cartridge 104. As shown in FIG. 7, in these examples, the control component may be implemented without switches Q1 and Q2 and capacitor C1, and the pull-up resistor R1 may be connected to the output of the authentication device. When the control body is uncoupled with the cartridge (in the standby mode), the pull-up resistor R1 is configured to cause a logical high level of voltage at the third positive conductor 604. That is, the pull-up resistor may be configured to pull the voltage at the third positive conductor toward the positive battery (power supply) voltage for the logical high level.

Also when the control body 102 is uncoupled with the cartridge 104, the authentication device 602 and the capacitor C2 connected to its output are respectively unpowered and uncharged. A coupling of the control body with the cartridge causes the voltage at the third positive conductor 604 to initially decrease from the logical high level to a logical low level corresponding to the approximately zero voltage of the capacitor. In response to this initial decrease in voltage at the third positive conductor, the microprocessor may be configured to control operation of a functional element. After the initial decrease in voltage at the third positive conductor, the positive battery (power supply) voltage may charge the capacitor to its final value, which may cause a corresponding increase in voltage at the third positive conductor.

Figure 8:
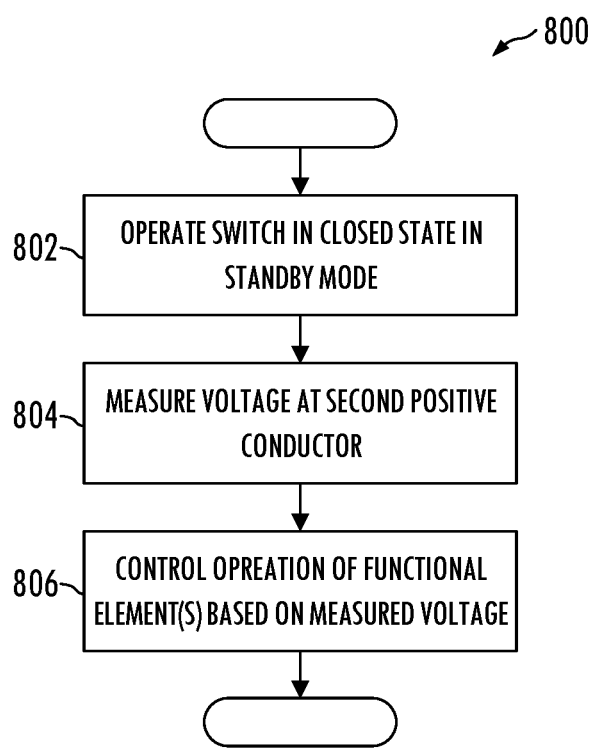
FIG. 8 illustrates various operations in a method of controlling a control body coupleable with a cartridge, according to example implementations.

FIG. 8 illustrates various operations in a method 800 of controlling the control body 102 coupleable with the cartridge 104 that is equipped with the heater 222 (heating element) and contains an aerosol precursor composition. As shown in block 802, the method includes operating the switch Q1 in a closed state in a standby mode in which the pull-up resistor R1 is configured to cause a logical high level of voltage at the second positive conductor 306 when the control body is uncoupled with the cartridge. Also in the standby mode, the heater is unpowered causes a logical low level of the voltage at the second positive conductor when the control body is coupled with the cartridge. The method also includes measuring the voltage at the second positive conductor, and controlling operation of at least one functional element of the aerosol delivery device based on the voltage measured at the second positive conductor, as shown in blocks 804 and 806.

In some examples, controlling operation of the at least one functional element includes controlling operation of the at least one functional element in response to a coupling of the control body 102 with the cartridge 104 that causes the voltage at the second positive conductor 306 to decrease from the logical high level to the logical low level. In some examples, controlling operation of the at least one functional element includes controlling operation of the at least one functional element in response to an uncoupling of the control body with the cartridge that causes the voltage at the second positive conductor to increase from the logical low level to the logical high level. And in some examples, controlling operation of at least one functional element includes controlling operation of at least one visual, audio or haptic indicator 312.

In some examples, the control body 102 further includes a voltage divider 314 connected to the second positive conductor and referenced to ground. In these examples, measuring the voltage at the second positive conductor may include measuring the voltage from the voltage divider.

In some examples, the control body 102 further includes a second switch Q2 connected to and between the voltage divider 314 and ground. In these examples, the method may further include operating the second switch in an open state in the standby mode.

In some further examples, the voltage divider 314 may include an output, and the control body 102 may further include a capacitor C1 connected to and between the output and ground. In these examples, measuring the voltage at the second positive conductor 306 may include measuring the voltage from the output of the voltage divider.

In some examples, the method further includes operating the switch Q1 in an open state in an active mode in which the control body 102 is coupled with the cartridge 104. In these examples, in the active mode, the method may even further include directing power to the heater 222 to activate and vaporize components of the aerosol precursor composition, with the voltage at the second positive conductor corresponds to a positive heater voltage. And in the active mode, the method may include measuring the positive heater voltage, and controlling the power directed to the heater based thereon.

In some examples in which the control body 102 further includes the voltage divider 314, measuring the positive heater voltage includes measuring the positive heating element voltage from the voltage divider. In these examples, the method may further include operating the second switch Q2 in a closed state in the active mode.

In some examples, directing power to the heater 222 and controlling the power directed to the heater includes at least directing power from the battery 212 to turn the heater on and commensurately initiate a heating time period. And at a periodic rate until expiration of the heating time period, the method may include determining a moving window of measurements of instantaneous actual power directed to the heater, with each measurement of the window of measurements being determined as a product of the positive heater voltage and a current through the heater. The method may include calculating a simple moving average power directed to the heater based on the moving window of measurements of instantaneous actual power, and comparing the simple moving average power to a selected power set point associated with the battery. And the method may include adjusting the power directed to the heater so as to turn the heater off or on at the periodic rate at each instance in which the simple moving average power is respectively above or below the selected power set point.

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIGS. 1-8 or as otherwise described above may be included in an aerosol delivery device according to the present disclosure.

Many modifications and other implementations of the disclosure set forth herein will come to mind to one skilled in the art to which these disclosure pertain having the benefit of the teachings presented in the foregoing descriptions and the associated drawings. Therefore, it is to be understood that the disclosure are not to be limited to the specific implementations disclosed and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method of controlling a control body coupleable with a cartridge that is equipped with an electrical load and contains an aerosol precursor composition, the control body being coupleable with the cartridge to form an aerosol delivery device in which the electrical load is configured to activate and vaporize components of the aerosol precursor composition, the control body including a first positive conductor connectable with a power source, a second positive conductor connectable with the electrical load, and a series pull-up resistor and switch connected to and between the first positive conductor and second positive conductor, the switch being connected to and between the pull-up resistor and second positive conductor, the method comprising:

operating the switch in a closed state in a standby mode in which the pull-up resistor is configured to cause a logical high level of voltage at the second positive conductor when the control body is uncoupled with the cartridge, and in which the electrical load is unpowered and causes a logical low level of the voltage at the second positive conductor when the control body is coupled with the cartridge;

measuring the voltage at the second positive conductor; and controlling operation of at least one functional element of the aerosol delivery device based on the voltage measured at the second positive conductor.

2. The method of claim 1, wherein controlling operation of the at least one functional element includes controlling operation of the at least one functional element in response to a coupling of the control body with the cartridge that causes the voltage at the second positive conductor to decrease from the logical high level to the logical low level.

3. The method of claim 1, wherein controlling operation of the at least one functional element includes controlling operation of the at least one functional element in response to an uncoupling of the control body with the cartridge that causes the voltage at the second positive conductor to increase from the logical low level to the logical high level.

4. The method of claim 1, wherein controlling operation of at least one functional element includes controlling operation of at least one visual, audio or haptic indicator.

5. The method of claim 1, wherein the control body further includes a voltage divider connected to the second positive conductor and referenced to ground, and
wherein measuring the voltage at the second positive conductor includes measuring the voltage from the voltage divider.

6. The method of claim 5, wherein the control body further includes a second switch connected to and between the voltage divider and ground, and
wherein the method further comprises operating the second switch in an open state in the standby mode.

7. The method of claim 5, wherein the voltage divider includes an output, and the control body further comprises a capacitor connected to and between the output and ground, and
wherein measuring the voltage at the second positive conductor includes measuring the voltage from the output of the voltage divider.

8. The method of claim 1 further comprising:
operating the switch in an open state in an active mode in which the control body is coupled with the cartridge; and in which the method further comprises,
directing power to the electrical load to activate and vaporize components of the aerosol precursor composition, and in which the voltage at the second positive conductor corresponds to a positive electrical load voltage;
measuring the positive electrical load voltage; and
controlling the power directed to the electrical load based thereon.

9. The method of claim 8, wherein the control body further includes a voltage divider connected to the second positive conductor and referenced to ground, and includes a second switch connected to and between the voltage divider and ground,
wherein measuring the positive electrical load voltage includes measuring the positive electrical load voltage from the voltage divider, and
wherein the method further comprises operating the second switch in a closed state in the active mode.

10. The method body of claim 8, wherein directing power to the electrical load and controlling the power directed to the electrical load includes at least:
directing power from the power source to turn the electrical load on and commensurately initiate a loading time period; and at a periodic rate until expiration of the loading time period,
determining a moving window of measurements of instantaneous actual power directed to the electrical load, each measurement of the window of measurements being determined as a product of the positive electrical load voltage and a current through the electrical load;
calculating a simple moving average power directed to the electrical load based on the moving window of measurements of instantaneous actual power;
comparing the simple moving average power to a selected power set point associated with the power source; and
adjusting the power directed to the electrical load so as to turn the electrical load off or on at the periodic rate at each instance in which the simple moving average power is respectively above or below the selected power set point.

11. The method of claim 1, wherein the electrical load comprises a heating element.

* * * * *